United States Patent [19]

Tamura

[11] Patent Number: 5,541,973

[45] Date of Patent: Jul. 30, 1996

[54] MICRO AREA ANALYZING METHOD

[75] Inventor: Kouichi Tamura, Chiba, Japan

[73] Assignee: Seiko Instruments Inc., Chiba, Japan

[21] Appl. No.: 412,665

[22] Filed: Mar. 29, 1995

[30] Foreign Application Priority Data

Apr. 1, 1994 [JP] Japan .................................. 6-065308

[51] Int. Cl.⁶ .................................................. G01N 23/223
[52] U.S. Cl. ............................................. 378/45; 378/48
[58] Field of Search ........................... 378/45, 44, 48

[56] References Cited

U.S. PATENT DOCUMENTS 5,062,127  10/1991  Sayama et al. .................. 378/48 X
5,422,925  6/1995  Komatsu et al. ..................... 378/45

*Primary Examiner*—David P. Porta
*Attorney, Agent, or Firm*—Loeb & Loeb LLP

[57] ABSTRACT

A method for analyzing a micro area in a micro area X-ray analyzing device which detects X-rays from a sample irradiated by a primary beam and analyzes the sample by analyzing spectra of the X-rays, which method includes selecting a combination of a plurality of stage positions in which an overlapped area of a plurality of primary beam spots nearly conforms with a predetermined analytical area, and calculating a common element of X-ray spectra acquired in the plural stage positions to obtain information on the predetermined analytical area and a background of the sample.

1 Claim, 4 Drawing Sheets

FIG. 3A I-J 

1

MICRO AREA ANALYZING METHOD

BACKGROUND OF THE INVENTION

This invention relates to an X-ray analyzing method for detecting an X-ray excited from a sample onto which an X-ray or an electron beam is irradiated, for analyzing elements of the sample.

Conventionally, it is impossible to analyze elements of a sample with a higher space resolution than a spot size of an X-ray or an electron beam which is used as a primary beam. Methods for creating a smaller spot size of the primary beam on the sample have accordingly been sought in the prior art. For example, when the X-ray is used as the primary beam, a method for collimating the primary beam with a collimator and limiting an irradiated area or a method for converging the primary beam with an X-ray optical system has been adopted. Further, when the electron beam is used as the primary beam, an electron optical system with a high accuracy is employed. However, the conventional methods have the following problems in case the X-ray is used as the primary beam.

The limit value of the spot size is only ten to several tens of μm, achieved with a micro area collimator for restricting the irradiated area, and the X-ray optical system requires sophisticated technology to produce X-ray optical parts. In addition, such a system is expensive and difficult to adjust. Further, the electron optical system is complex, expensive and large although it is effective to converge the beam.

Therefore, it is an object herein to analyze a smaller area than the spot size of the primary beam without making the spot size of the primary beam comparably small, so as to solve the problems in the prior art.

SUMMARY OF THE INVENTION

In order to solve the problems in the prior art, in an X-ray analyzing method wherein a sample is excited with an X-ray or an electron beam, resulting in the emission of X-rays which are detected and elements of the sample are analyzed, the X-ray analyzing method according to the present invention utilizes a sample stage having a minimum stroke which is smaller than the spot size of the primary beam and comprises the following steps:

1. selecting a combination of a first plurality of stage positions in which an overlapped area of a plurality of beam spots nearly conforms with a predetermined analytical area from the first plurality of stage positions in which the predetermined analytical area inscribes the primary beam spot areas, and obtaining a common element I of X-ray spectra acquired in the first plurality of stage positions;

2. selecting a combination of a second plurality of stage positions in which an overlapped area of a plurality of beam spots corresponding to the plurality of stage positions nearly conforms to a predetermined analytical area from the second plurality of stage positions, in which a condition that primary beam spot areas circumscribe a predetermined analytical area is satisfied, and obtaining a common element J of X-ray spectra acquired in the second plurality of stage positions; and 3. Obtaining the difference between the common element I and the common element J.

In the X-ray analyzing method according to the above method, the first common element of the plurality of spectra, which are obtained in the stage positions wherein the areas on the sample irradiated by the primary beam are inscribed by the analytical area, gives information of both the analytical area and a background in the vicinity of the analytical area. Further, the second common element of the plurality of spectra, which are obtained in the stage positions wherein the areas on the sample irradiated by the primary beam circumscribe the analytical area, gives information of a background without the analytical area in the vicinity of the analytical area. Only information of the analytical area is consequently obtained from the difference between the first and second common elements. In this case, a sample stage having a positioning error which is smaller than the size of the analytical area enables the X-ray analyzing device to analyze an area smaller than the spot size of the primary beam.

BRIEF DESCRIPTION OF THE DRAWING

FIGS. 3A and 3B are diagrams further illustrating the micro area analyzing according to the present invention.

DESCRIPTION OF THE PREFERRED EMBODIMENTS

An embodiment of the present invention will be described below with reference to drawings.

Figure 4:
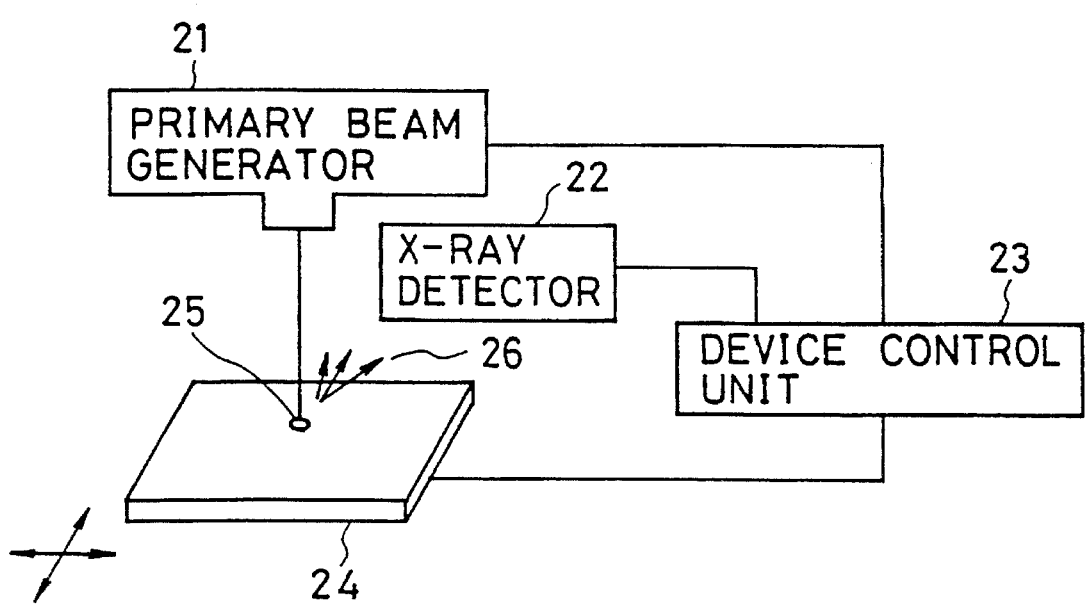
FIG. 4 is a schematic diagram of an X-ray analyzing device for implementing the present invention.

FIG. 4 is an example of the X-ray analyzing device utilized in the present invention. A sample stage 24 having a minimum displacement step, or stroke, which is smaller than the spot size of a primary beam is controlled for displacement in two mutually transverse, preferably mutually perpendicular, directions in a plane by a device control unit 23 so that the relative position between an irradiated area and an analytical area may optionally be selected. A primary beam from a primary beam generator 21 excites sample 25 on the sample stage 24, resulting in the generation of X-rays. The X-rays are detected by an X-ray detector 22 and the energy of the generated X-rays is discriminated by a conventional data processor 26 so as to obtain X-ray spectra. An X-ray beam or an electron beam is used as the primary beam. Each of the components shown in FIG. 4 can be a known component.

Figure 1A:
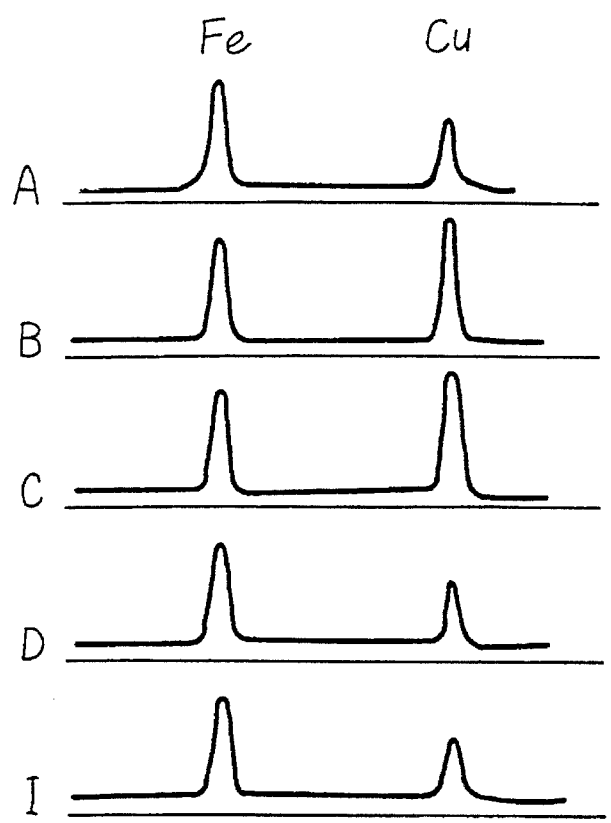
FIGS. 1A and 1B are diagrams illustrating the micro area analyzing method according to the present invention.
Figure 1B:
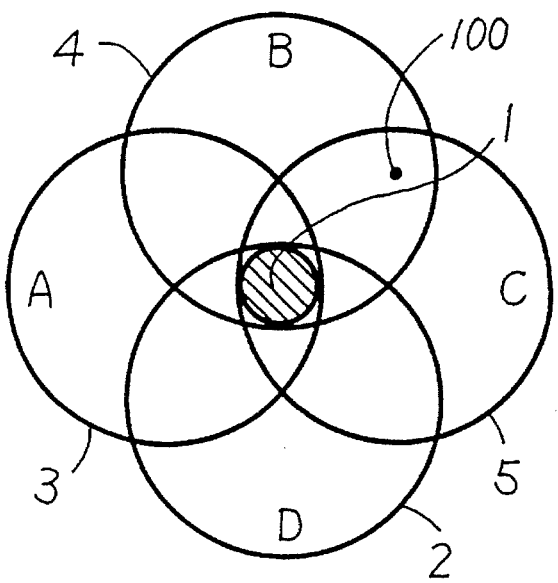

FIG. 1B is a schematic diagram showing, in the plane of displacement of stage 24, the position relation between four areas A, B, C, D irradiated in succession by the primary beam, and further showing a predetermined analytical area 1. Areas D, A, B, and C have outer peripheries 2, 3, 4 and 5, respectively.

First, stage 24 is moved to a position where, for example, area D irradiated by the primary beam is inscribed by the analytical area 1, and an X-ray spectrum is obtained at that position. The position relations between the periphery of the irradiated area and the analytical area 1 is illustrated in FIG. 1B. The shape and size of the irradiated area is measured in advance by the knife edge method on a Faraday cup in case the primary beam is an electron beam, or with a measuring method using sensitive films in case an X-ray beam is used as the primary beam. The method to obtain the irradiated size by detecting X-rays from the sample during scanning the sample stage is available in each case where an electron beam or an X-ray is employed as the primary beam.

For other stage positions where the irradiated areas are inscribed by the analytical area, X-ray spectra are also obtained. For example, the peripheries 3, 4, 5 of the irradiating areas A, B and C in the other positions are inscribed by the analytical area 1 in FIG. 1B. The sample stage is positioned so that the overlapped area of these irradiated areas nearly conforms with the analytical area 1. The acquisition of X-ray spectra may be done in at least three positions by appropriate selection of the irradiated areas although FIG. 1A shows the X-ray spectra obtained from four different positions. Then, a common element spectrum I is obtained from the plural X-ray spectra acquired in the plural positions. The minimum value of the spectra is selected regarding X-ray energy or channel. The spectra of the irradiated areas A, B, C, D and the common element spectrum I (element included commonly in the areas A, B, C, D) are shown in FIG. 1A.

A dust particle 100 is assumed to be present at the location shown in FIG. 1B. No dust exists in the areas A and D in FIG. 1B, so that both an iron spectrum, the iron being presumed as background, and a copper spectrum, the copper being presumed as a foreign matter in the analytical area, emerge in both spectrum A and spectrum D in FIG. 1A. Dust particle 100 is present in the overlapping portion of irradiated areas B and C, so that if the dust is a copper particle, the copper spectral line is intensified in the spectra for areas B and C as illustrated in FIG. 1A. The common elements existing in each spectrum A, B, C, D appear in spectrum I in FIG. 1A. Spectrum I obtained in this manner contains information regarding the background (iron in FIGS. 1) which exists uniformly in the vicinity of the analytical area because information regarding dust, stains, aggregations, etc. which locally exist outside of the analytical area 1 is canceled.

Figure 2A:
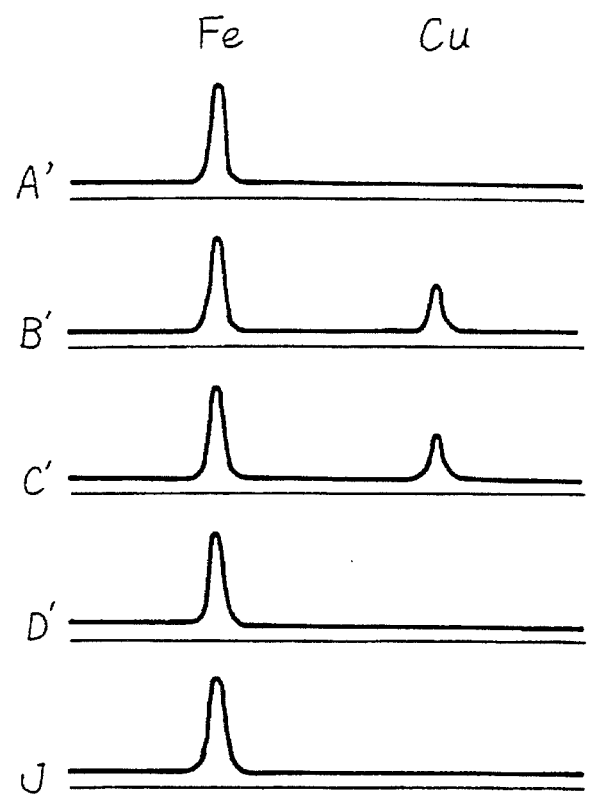
FIGS. 2A and 2B are diagrams similar to those of FIGS. 1A and 1B further illustrating the micro area analyzing according to the present invention.
Figure 2B:
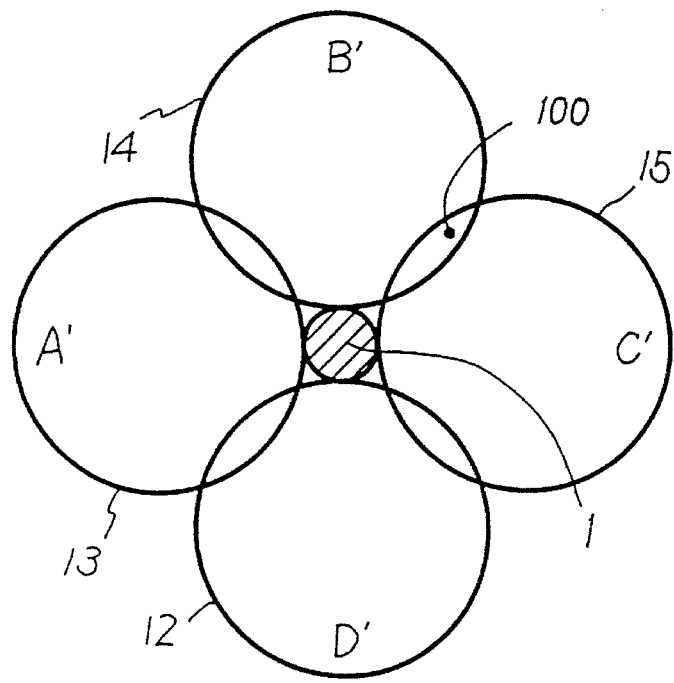

Second, the sample stage is moved so that the areas irradiated by the primary beam circumscribe, and essentially exclude, the analytical area 1 to obtain new X-ray spectra. FIG. 2B schematically illustrates position relations between irradiated areas A', B', C', D' and the analytical area 1, periphery 12 of the area A irradiated by the primary beam externally touching the analytical area 1.

There are other plural positions where the irradiated areas circumscribe the analytical area 1 as well as in case of inscribing, so that X-ray spectra are obtained from the other plural positions one by one. For example, the peripheries 13, 14, 15 of the irradiated areas B, C, D in the other positions circumscribe the analytical area 1 in FIG. 2B. The sample stage is positioned so that the area enclosed by the irradiated areas 12, 13, 14, 15 nearly conforms with the analytical area 1. The acquisition of X-ray spectra may be done at at least three positions by appropriate selection of the irradiated areas although the X-ray spectra are obtained in four different positions in FIGS. 2.

In this case as well as the above case, a common element spectrum J is obtained from the plural X-ray spectra acquired in the plural positions, and the same operation as that employed in case of obtaining the common element spectrum I is used. The spectra of the irradiated areas A', B', C', D' and the common element spectrum J are shown in FIG. 2A. No dust exists in the irradiated areas A' and D' in FIG. 2B, so that only the iron spectral line, iron being presumed as background, emerge in both spectra A' and D' in FIG. 2A. There exists dust in the irradiated areas B', C', so that if the dust is copper, the copper spectral line appears in the spectra for B' and C' as illustrated in FIG. 2A. Common elements existing in spectra A', B', C', D' appear in spectrum J in FIG. 2A. The common element spectrum J obtained in this manner includes no information on the analytical area 1 but includes only information on the background which exists uniformly in the vicinity of the analytical area because information regarding dust, stains, aggregations, etc. which locally exist outside of the analytical area 1 is canceled. The difference between the common element spectrum I and the common element spectrum J accordingly yields information on the analytical area 1 alone.

Figure 3B:
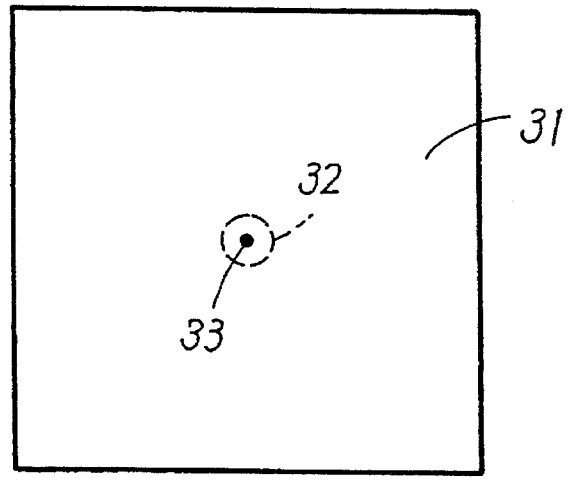

FIG. 3A illustrates a spectrum showing the difference I–J and teaches us there exists some quantity of copper in the analytical area 1, e.g. the existence of a copper grain 33 in the analytical area 32 of the iron background 31 as illustrated in FIG. 3B.

In this method, the area size that can be analyzed is determined by the minimum stroke and the positioning accuracy of the sample stage which moves the sample two-dimensionally. This method accordingly enables the micro analyzing device to analyze an area smaller than the spot size of the primary beam when the minimum stroke of the sample stage is smaller than the spot size of the primary beam.

The present invention results in an excellent effectiveness in micro area analyzing such as inspection of small-size foreign matters, material aggregation analysis, utilizing an X-ray analyzing system which analyzes elements of a sample by detecting X-rays generated from the X-ray or electron beam irradiated sample.

Especially, when using an X-ray primary beam, the cost of apparatus which converges a primary X-ray beam to a spot size smaller than 50 μm is unacceptably high, and it was thus very difficult to analyze such a small area by prior art techniques. However, the present invention makes possible micro area analysis with inexpensive equipment. Further, the present invention enables analysis of an area much smaller than 50 μm with equipment using a highly converged primary beam.

This application relates to subject matter disclosed in Japanese Application number 6-65306, filed on Apr. 1, 1994, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A micro area analyzing method for analyzing an area of a sample, the area having a sample area size, by projecting a primary beam having a spot with a spot size larger than the sample area size while the sample is mounted on a surface of a sample stage, the primary beam exciting emission from the sample of X-rays having a spectrum, said method comprising the steps of:

a) placing the primary beam in a plurality of first positions in succession relative to the surface to cause the beam to form a plurality of spots all of which overlap in an area which conforms closely to the area of the sample, detecting X-rays excited by the primary beam at each of the first positions, deriving first X-ray spectra each based on the detected X-rays excited by the primary beam at each of the first positions, and obtaining a first common X-ray spectrum containing only spectral components which appear in all of the derived first X-ray spectra;

b) placing the primary beam in a plurality of second positions in succession relative to the surface to cause the beam to form a plurality of spots which surround the area of the sample and which do not overlap the area of the sample, detecting X-rays excited by the primary beam at each of the second positions, deriving second X-ray spectra each based on the detected X-rays excited by the primary beam at each of the second positions, and obtaining a second common X-ray spectrum containing only spectral components which appear in all of the derived second X-ray spectra; and c) determining the difference between the first common X-ray spectrum and the second common X-ray spectrum.

\* \* \* \* \*